United States Patent [19]
Hsieh et al.

[11] Patent Number: 5,271,055
[45] Date of Patent: Dec. 14, 1993

[54] METHODS FOR REDUCING MOTION INDUCED ARTIFACTS IN A PROJECTION IMAGING SYSTEM

[75] Inventors: Jiang Hsieh, Waukesha; Michael F. Gard, New Berlin, both of Wis.; Cameron J. Ritchie, Seattle, Wash.

[73] Assignee: General Electric Company, Milwaukee, Wis.

[21] Appl. No.: 932,446

[22] Filed: Aug. 19, 1992

[51] Int. Cl.$^5$ .............................................. H05G 1/10
[52] U.S. Cl. ........................................ 378/95; 378/8; 364/413.13
[58] Field of Search .................... 324/309, 307; 378/8, 378/4, 20, 95, 106; 364/413.13–413.15

[56] References Cited

U.S. PATENT DOCUMENTS

| | | | |
|---|---|---|---|
| 4,182,311 | 1/1980 | Seppi et al. | 378/8 |
| 4,387,722 | 6/1983 | Kearns | 378/95 |
| 4,530,109 | 7/1985 | Klausz | 378/8 |
| 4,547,892 | 10/1985 | Richey et al. | 378/8 |
| 4,751,462 | 6/1988 | Glover et al. | 324/309 |
| 4,994,965 | 2/1991 | Crawford et al. | 364/413.15 |
| 5,040,201 | 8/1991 | Slump | 378/95 |
| 5,067,494 | 11/1991 | Rienmueller et al. | 378/8 |

Primary Examiner—David P. Porta
Attorney, Agent, or Firm—Quarles & Brady

[57] ABSTRACT

A medical imaging system has a source of X-rays and a detector which produces an electrical signal in response to X-rays. A signal generated by the detector, during an acquisition interval, is used to construct an image of a medical patient, which may contain artifacts due to motion of patient. A signal is produced indicative of the motion, which has a quiescent period of minimum movement. A first portion of the signal is selected such that if image acquisition commenced at the end of the first portion, the acquisition interval would occur during a quiescent period. This first portion is initially used as a reference signal portion. Then subsequent portions of the signal are compared to the reference signal portion to produce a descriptor of the degree of similarity. An image acquisition is commenced when the descriptor indicates a given degree of similarity that is above a defined threshold. Periodically a subsequent portion of the signal is combined with the previous reference signal portion to create an updated reference signal portion which thereafter is used in the comparison step.

18 Claims, 3 Drawing Sheets

METHODS FOR REDUCING MOTION INDUCED ARTIFACTS IN A PROJECTION IMAGING SYSTEM

BACKGROUND OF THE INVENTION

The present invention relates to medical imaging systems such as X-ray equipment, computed tomography imaging apparatus and magnetic resonance imagers, and more particularly, to techniques for removing image artifacts that are produced by movement of the patient.

For example, in a computed tomography system an X-ray source projects a fan-shaped beam which is collimated to lie within an X-Y plane of a Cartesian coordinate system, termed the "imaging plane". The X-ray beam passes through the object being imaged, such as a medical patient, and impinges upon an array of radiation detectors. The intensity of the transmitted radiation is dependent upon the attenuation of the X-ray beam by the patient and each detector produces a separate electrical signal that is a measurement of beam attenuation along a specific ray path. The attenuation measurements from all the detectors are acquired separately to produce the transmission profile.

The source and detector array in a common type of CT system are rotated on a gantry within the imaging plane and around the patient so that the angle at which the X-ray beam intersects the patient constantly changes. A group of X-ray attenuation measurements from the detector array at a given angle is referred to as a "view" and a "scan" of the patient comprises a set of views made at different angular orientations during one revolution of the X-ray source and detector. The gantry may stop or continue to move as the measurements are being made. The image produced from the scan data correspond to a two dimensional slice taken through the patient.

Typical CT systems may be operated in either the axial mode or the helical scan mode. In the typical axial mode, the patient being imaged remains stationary during each scan and the gantry revolves once to complete a scan. The gantry may make additional revolutions to acquire image data at the same slice position through the patient in order to observe temporal changes, such as occur in the heart at different stages of the cardiac cycle. The patient may also be moved between rotations in order to observe different slices through the patient. In the conventional helical scan mode, the gantry with the X-ray source and detector array revolves continuously while the patient is translated through the imaging plane. Each revolution of the gantry, or scan, acquires projection data through the patient in three dimensions in a single operation. These data are processed subsequently to form the desired image plane through the patient.

The resultant set of projections from a scan are used to reconstruct an image which reveals the anatomical structures at the position of each slice taken through the patient. The prevailing method for image reconstruction image is referred to in the art as the filtered back-projection technique. This process converts the attenuation measurements from a scan into integers called "CT numbers" or "Hounsfield units", which are used to control the brightness of a corresponding pixel on a cathode ray tube display.

It is well recognized that artifacts caused by patient movement are limiting factors in the imaging of small structures in the chest and abdomen. Normal motion of the chest wall and diaphragm during breathing causes movement of internal organs during the scan interval. Such movement changes the shape of the imaged object during the scan and thereby produces blurring, streaking, dark bands and voids, and anatomical distortion in the reconstructed image.

Presently it is a common clinical practice to request a patient to hold his or her breath during the CT scan to alleviate motion artifacts. Although this can be done by a cooperative patient, it may not be possible in subjects with serious disease who are incapable of holding their breath for all but the shortest durations. A voluntary breath hold is out of the question for pediatric procedures, or when the patient is uncooperative or unconscious as in trauma cases.

A technique for acquiring motion-free images from uncooperative patients is to employ physiological gating of the imaging scan. One such approach is described in U.S. Pat. No. 4,994,965 in which the image acquisition interval is centered within a quiescent period of the periodic motion. Quiescent periods occur during the respiratory cycle at the ends of expiration and inspiration. The chest anatomy is well separated in an image acquired at the end of inspiration, whereas the end of expiration is preferred for abdominal imaging. Methods, such as the one disclosed in the above-referenced U.S. patent, have been devised to predict the approach of the quiescent period for the purpose of initiating the image scan. However, these prior prediction methods assumed that respiration was a periodic function.

The present inventors through experimentation have determined that human respiration is not periodic and can vary markedly over several breathing cycles. In addition, the amplitude of lung expansion and therefore the motion of other organs varies significantly from breath to breath. Thus, techniques based on the assumption that respiration is a periodic physiological function or based on the magnitude of patient movement may not always gate image acquisition at the optimum point in time.

SUMMARY OF THE INVENTION

A medical imaging apparatus produces an image of the patient from data obtained during an image acquisition interval. In many instances, the image acquisition interval is of such duration that physiological motion causes artifacts in the image. Certain physiological activities, such as respiration, have irregularly occurring quiescent periods of minimal movement during which it is desirable to perform image data acquisition. However, the image data acquisition must be started in advance of the actual quiescent period in order to obtain maximum benefit from the patient's reduced level of motion.

A method for reducing artifacts due to object motion comprises producing a signal indicative of the motion. A point is defined in the signal such that, if image acquisition commenced at that point, a quiescent period would occur during the resultant image acquisition interval. An analysis of the shape of the signal waveform is performed using an adaptive shape criterion that is updated over time, and is based on information from the actual patient motion signal. The results of the analysis are employed to predict the approach of a quiescent period, and image acquisition is started at a time prior to the predicted quiescent period so that data acquisition will occur during the quiescent period.

In the preferred embodiment, the signal indicative of the motion is digitized into a series of signal samples and a benchmark signal sample which occurred during a known quiescent period is identified. From this benchmark signal sample, the preferred embodiment identifies a particular signal sample, $k_{end}$, that was acquired a known number of samples before the benchmark signal sample. Sample $k_{end}$ has the property such that if image acquisition had commenced when that motion signal sample was acquired, a quiescent period would occur during the acquisition interval. The group of the signal samples acquired immediately prior to sample $k_{end}$ are used to form a correlation kernel. Thereafter, other groups of signal samples are compared to the correlation kernel and used to produce an descriptor of the similarity between the two signal sample groups. Image data acquisition is initiated when the descriptor indicates at least a given degree of similarity exists.

An object of the present invention is to provide a process for predicting the occurrence of a quiescent interval of aperiodic physiological activity. The prediction is made sufficiently prior to the quiescent period that the period will occur during image data acquisition.

Another object is to provide a prediction technique which adapts to variations of the physiological activity.

A further object is to provide a prediction technique in which aberrations in the physiological activity will have minimal effect on accuracy of the prediction.

DETAILED DESCRIPTION OF THE INVENTION

Figure 1:
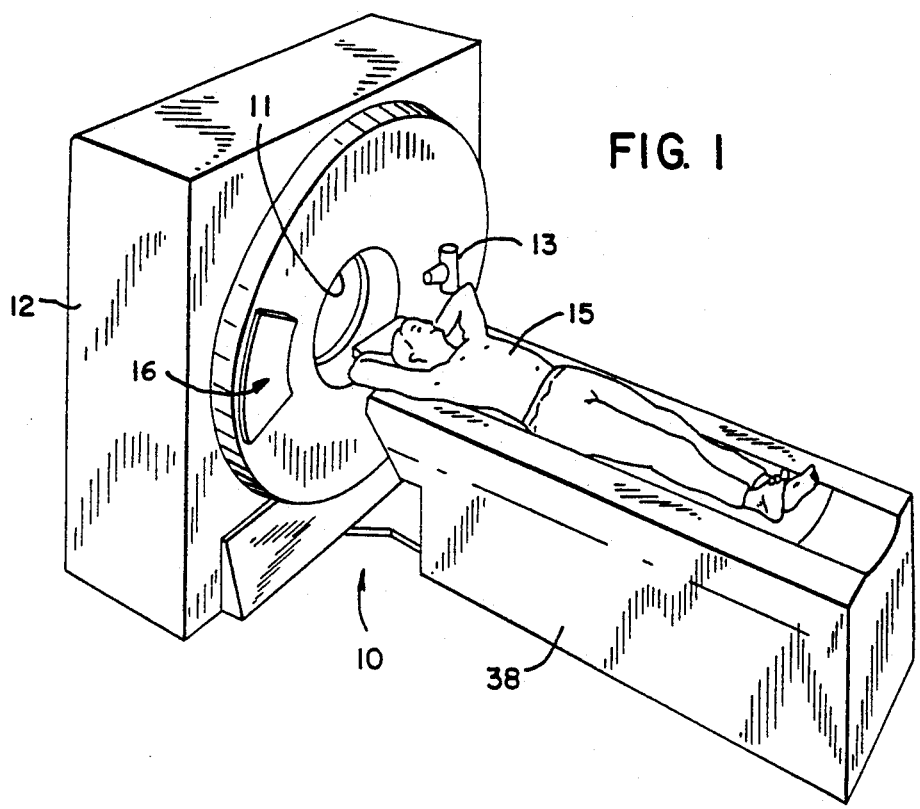
FIG. 1 is a pictorial view of a CT imaging system in which the present invention may be employed.
Figure 2:
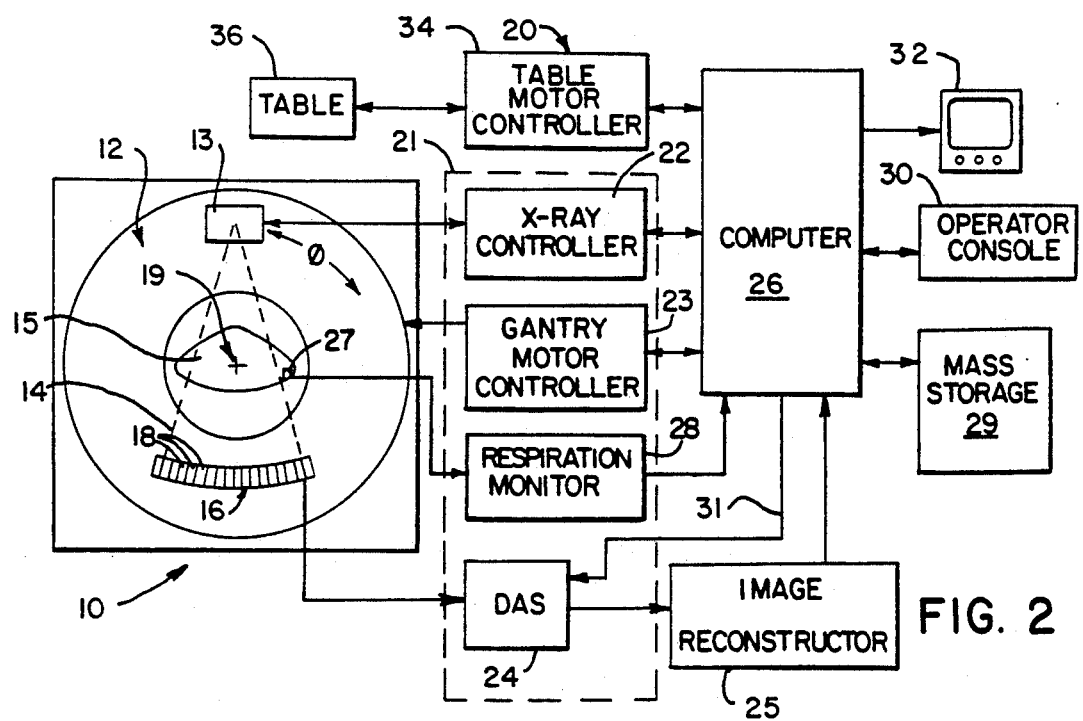
FIG. 2 is a block schematic diagram of a CT apparatus.

With initial reference to FIGS. 1 and 2, a computed tomography (CT) imaging system 10 includes a gantry 12 representative of a "third generation" CT scanner. The gantry 12 includes an X-ray source 13 oriented to project a fan beam of X-rays 14 through imaged patient 15 to detector array 16. The detector array 16 is formed by a number of detector elements 18 which together detect a projected image resulting from the transmission of X-rays through the imaged object 15, such as a medical patient. The gantry 12 and the components mounted thereon rotate about a center of rotation 19 normally located within the patient 15.

A control mechanism 20 of the CT system 10 has gantry associated control modules 21 which include an X-ray controller 22 which provides power and timing signals to the X-ray source 13, a gantry motor controller 23 that controls the rotational speed and position of the gantry 12, and a data acquisition system (DAS) 24 which samples projection data from detector elements 18 and converts the data to digital words for later computer processing.

The data acquisition system 24 filters, amplifies, digitizes and otherwise conditions the signal from each detector element 18. However, a single or a small number of such digitizing circuits can be provided with the individual signals from the detector elements 18 being time division multiplexed into that circuit, as was done in previous systems. A data output from the DAS 24 is connected to image reconstructor 25 which receives sampled and digitized projection data from the DAS 24 and performs high speed image reconstruction according to methods known in the art. The image reconstructor 25 may be an array processor, such as one manufactured by Star Technologies.

The X-ray controller 22 and the gantry motor controller 23 are connected to a computer 26, such as a Data General Eclipse MV/7800C general purpose minicomputer, which provides processing data and control signals to DAS 24 via buses 31. The computer 26 receives commands and scanning parameters via an operator console 30 that has a cathode ray tube display and keyboard which allows the operator to enter parameters for the scan and observe the reconstructed image and other information from the computer. A mass storage device 29 provides a means for storing operating programs for the CT imaging system, as well as image data for future reference by the operator. A separate high resolution video monitor 32 is provided to display the reconstructed image of the patient 15.

The image data acquisition is gated by a physiological phenomenon which is detected by a sensor 27 attached to the patient. For example, the sensor 27 may be a piezoelectric strip attached to the patient's chest to produce an electrical signal representing movement of the patient's chest and indicative of respiration. The piezoelectric strip is a thin piezoelectric crystal, such as one made by Medasonics of Fremont, Calif., that generates a voltage when it is mechanically deformed. This type of sensor 27 generates relatively large signals from small deformations. The sensor 27 is connected to a respiration monitor 28 which includes conventional circuitry for driving the piezoelectric crystal and receiving the output signal. As the output from the piezoelectric crystal is a derivative of the chest wall position in this example, the respiration monitor 28 must integrate the signal to obtain the position information which then is digitized for input into the computer 26.

Alternatively the sensor 27 may comprise a strain gauge, a linear variable displacement transducer (LVDT), an ultrasonic time-of-flight transducer, an infrared triangulation device, or other technology. Whichever type of sensor 27 is employed, its output signal is applied to an appropriate respiration monitor to produce digital data representing the position of the patient's chest during each respiration cycle.

Figure 3:
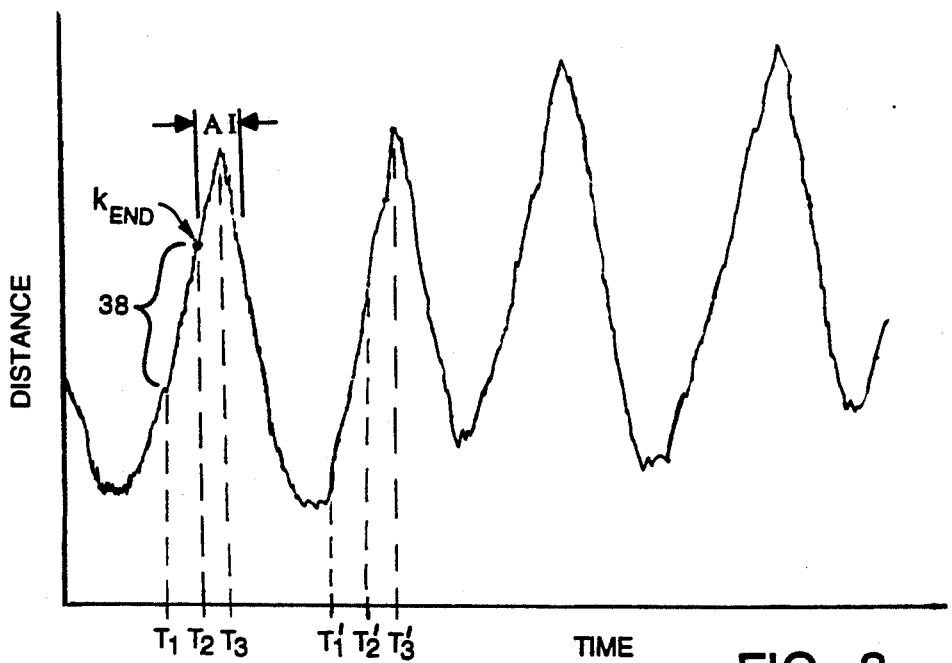
FIG. 3 is an exemplary waveform of the signal produced by a respiration monitor in the CT apparatus.

FIG. 3 depicts an exemplary signal waveform from the respiration monitor 28. As noted previously, the respiration signal varies from patient to patient and the magnitude and period of the signal from the same patient may vary widely over a several respiration cycles. To minimize motion artifacts in the image, the image should be acquired during quiescent periods of the respiration cycle which occur at the peaks and valleys in the signal waveform. In order to center the image acquisition interval (AI) about the end of inspiration, shown as a waveform peak in FIG. 3, it is necessary to commence the CT scan at a time T2 prior to the end of inspiration (time T3) during one of the respiration cycles. Thus, the gating system must be able to predict the end of inspiration in order to start the scan at time T2. The period between time T2 and the middle of the acquisition interval T3 depends upon the duration of the acquisition interval, and the delay between a start command from the operator and initiation of data acquisition of the particular CT system. These periods can be determined experimentally for a given type of system.

Figure 4A:
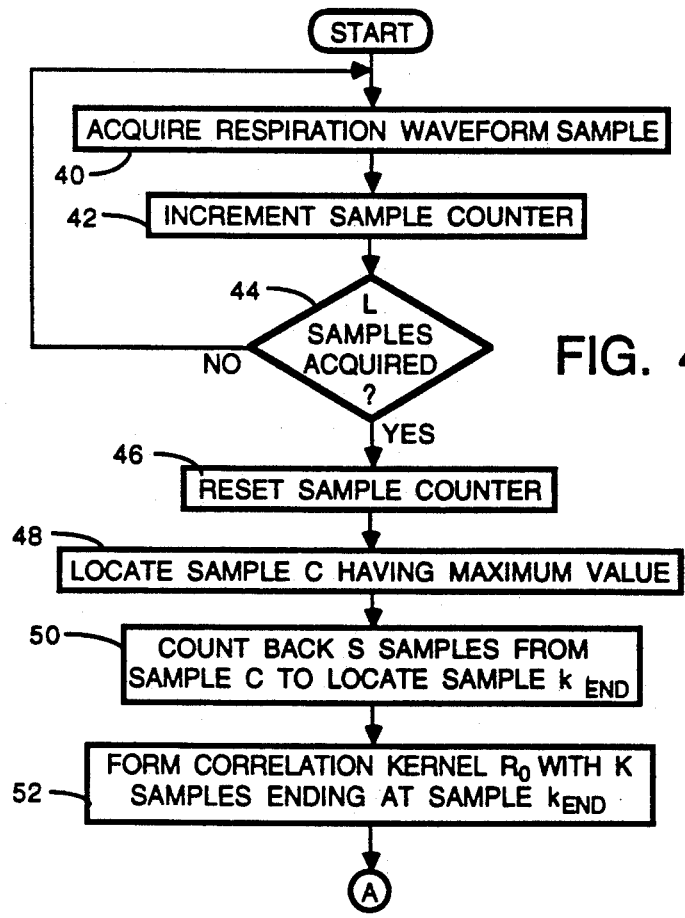
FIGS. 4A and 4B are a flowchart of a program that acquires and analyzes the respiratory waveform to determine when to initiate image data acquisition.

When the operator signals via the console 30 that a patient is connected to the monitor 28, the computer 26 begins acquiring digital samples of the respiration waveform from monitor 28. The respiration waveform is sampled approximately 75 times per second, for example. Even though the operator has yet to request a CT image scan, the computer 26 begins executing a software routine depicted by the flowchart of FIG. 4A which analyzes the signal samples to find time T2 during every respiration cycle. At steps 40, 42 and 44, the computer 26 acquires signal samples from the respiration monitor 28 during at least one respiration cycle of the patient. The program execution continues to loop through steps 40-44 until L number of respiration signal samples have been obtained. The value of number L can be defined by the operator to insure a sufficient number of samples are acquired even from patients with abnormally long respiration cycles. This acquisition process creates a block of data having L ordered pairs comprising a sample number and a waveform value. Once L samples have been acquired, the program execution advances to step 46 where a sample counter is reset to zero.

Then at step 48, the waveform values in the block of data are compared to find the one having the maximum value. A filter may be applied to the input signal to reduce the statistical fluctuation of the respiratory waveform. In this example, the maximum sample corresponds to an end of inspiration and the computer 26 records the sample number of the ordered pair which has the maximum waveform value. Based on the number of samples per second, the microcomputer at step 50 counts back a number of samples S from the sample which occurred at the end of inspiration. S corresponds to the number of samples which occur during the interval between CT scan initiation and the middle of the acquisition interval AI in FIG. 3. The number of samples S is given by:

$$S = \frac{\frac{AI}{2} + \text{set up time}}{T_{samp}} \quad (1)$$

where AI is the image acquisition interval and the setup time is the period between when the gantry motor controller 23 and the X-ray controller 22 receive a scan start command and when actual X-ray production occurs at the beginning of image data acquisition. $T_{samp}$ is the reciprocal of the sampling rate. Thus, the number S represents, in samples, how far in advance the system needs to be started in order to center the image data acquisition interval on the end of inspiration. The sample at this point is labelled as $k_{end}$.

A first portion 38 of the waveform prior to sample $k_{end}$ is used as a signature of the waveform to identify when the CT scanning process must be started in order to center the data acquisition interval AI about the end of inspiration. This first portion 38 is compared with sets of more current respiration samples that form other portions of the respiration waveform, and when a high degree of fit occurs between the two portions the system determines that time T2' has occurred for that respiration cycle. The degree of fit can be determined by several techniques, the preferable one being a correlation. This technique uses an adaptive correlation kernel representing the portion of the respiration waveform immediately preceding the point at which the scan must be initiated.

The sample $k_{end}$ corresponds to the last sample point in the correlation kernel. The length of this correlation kernel is determined by the expression:

$$K = 2\left(\frac{\beta}{T_{samp}}\right) + 1 \quad (2)$$

where K is the kernel length in samples and $\beta$ is a predictor accuracy factor. The value of $\beta$ determines the tradeoff between predictor accuracy and computation time. For example, a value for $\beta$ of 0.07 may be used in the adaptive moving correlation technique for CT respiratory gating. Adding one to the expression insures that the kernel length always will be an odd number of samples.

Once $k_{end}$ and K are known, the K samples immediately preceding $k_{end}$, waveform portion 38, are obtained at step 52 and placed in a one-dimensional array that corresponds to the first correlation kernel, $R_0$ (where bold type indicates a vector).

Figure 4B:
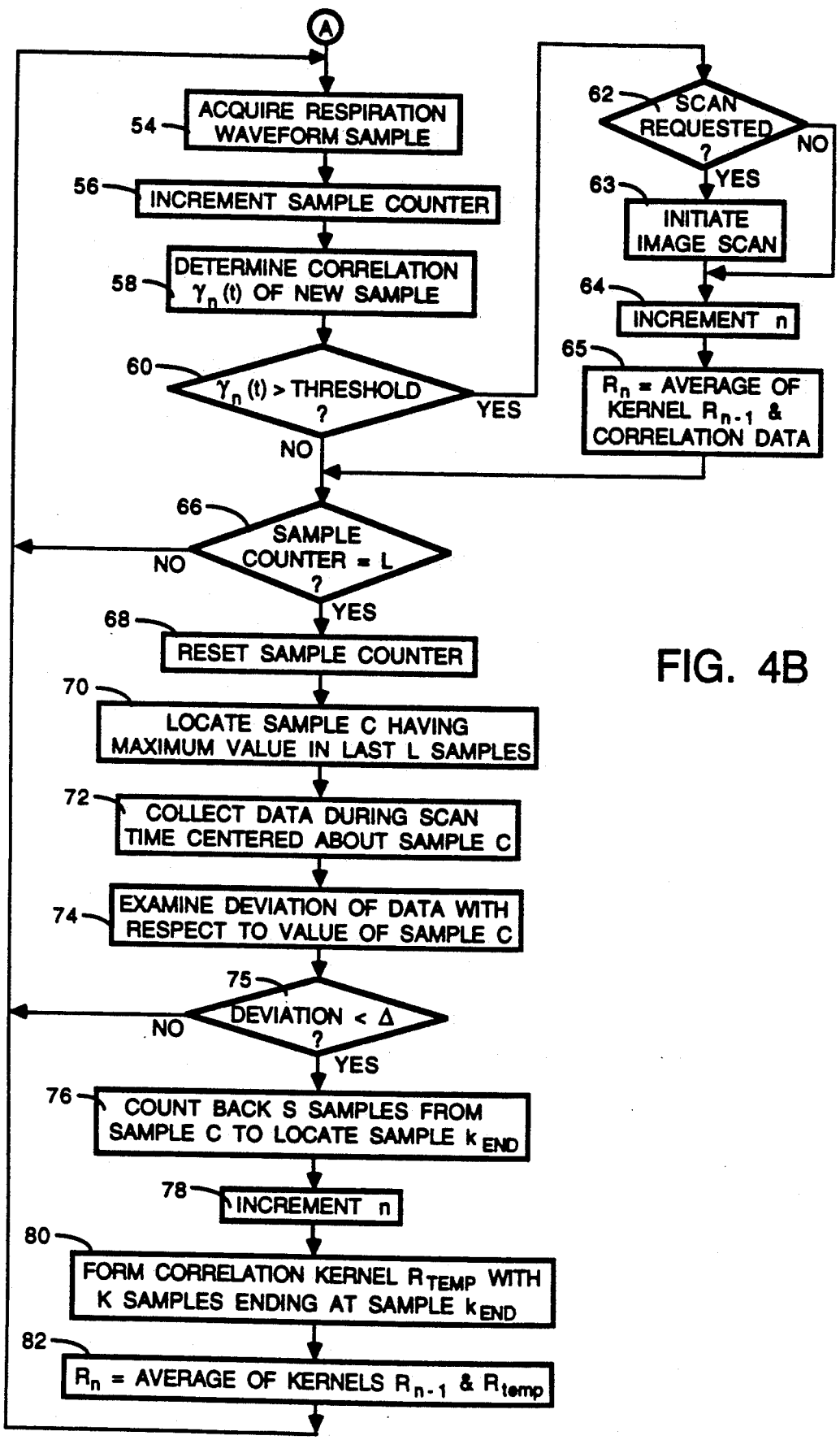

The program execution by computer 26 advances to step 54 on FIG. 4B at which point another sample of the respiration waveform is acquired and stored in memory with the previously acquired samples. The sample counter is incremented at step 56. The kernel $R_0$ then is correlated with the respiration waveform function each time a new sample is acquired, starting with the first sample read after the initial block of data at step 58. The correlation of two continuous functions is defined as:

$$\gamma_n(\tau) = \frac{\int_{t_1}^{t_2} f_1(t) R_n(t - \tau) dt}{\sqrt{\int_{t_1}^{t_2} f_1^2(t) dt \int_{t_1}^{t_2} R_n^2(t - \tau) dt}} \quad (3)$$

where $\gamma_n(\tau)$ is the correlation at a temporal separation of $\tau$ samples, $f_1$ is the last K samples of the respiration waveform, and t is a dummy variable. A correlation between two sets of respiration samples is defined as equal to +1 when the corresponding waveform portions are identical, and −1 when the portions are opposite (i.e. identical except for a sign change).

The corresponding discrete form of equation (3) is:

$$\gamma_n(K) = \frac{\sum_m f_1(m) R_n(m - K)}{\sqrt{\sum_m f_1^2(m) \sum_{m'} R_n^2(m' - K)}} \quad (4)$$

Alternatively, the mean of each function can be removed to compute the correlation:

$$\gamma_n(\tau) = \frac{\int_{t_1}^{t_2} (f_1(t) - m_f)[R_n(t - \tau_n) - m_R] dt}{\sqrt{\int_{t_1}^{t_2} [f_1(t) - m_f]^2 dt \int_{t_1}^{t_2} [R_n(t - \tau) - m_R]^2 dt}} \quad (5)$$

where $m_f$ and $m_R$ are the means of $f_1(t)$ and $R_n(t - \tau_n)$ for the time interval $[t_1, t_2]$, respectively.

The correlation value $\gamma_n(\tau)$ is compared to a threshold at step 60. A correlation greater than the threshold (e.g. 0.99) indicates that a sample corresponding to $k_{end}$ in the next cycle of the respiration waveform has just been acquired and an image scan can be commenced if desired. When the degree of correlation is insufficient, the program execution advances directly to step 66. However, if the correlation exceeds the threshold, the computer 26 tests the operator console input to detect if the operator has requested an image scan at step 62. If a scan request has been made, the program execution branches to step 63 where the computer 26 sends commands to the X-ray controller 22 and the gantry motor controller 23 to begin the scan. The correlation kernel is now updated by first incrementing the kernel count n at step 64. Then a new kernel $R_n$ is formed at step 65 by weighted averaging the previous kernel $R_{n-1}$ with the data used in step 58 to determine the correlation of the new sample. The program execution by the computer 26 then advances to step 66.

The present process adapts the correlation kernel to changes in the respiration pattern of the patient and also reduces effects that aberrations in the patient's respiration would otherwise have on the kernel. For example, if the initial kernel $R_0$ was formed from an block of data that happened to be acquired at a time when the patient was coughing or otherwise moving, it is conceivable that a correlation greater than the threshold based on that kernel will never occur. To account for this possibility, the correlation kernel is updated periodically.

Beginning at step 66, a determination is made whether the correlation kernel should be updated. The updating occurs when another L number of samples have been acquired since the last update and when the relevant portion of the respiration signal has a sufficiently reliable correlation to the previous kernel. The sample counter is examined to detect whether an addition L samples have been acquired at step 66. If not, the program execution returns to step 54 to acquire another sample of the respiration signal.

When a sufficient number of samples have been acquired, the program advances to step 68 where the computer 26 resets the sample counter to zero. Then at step 70, the group of the last L respiratory samples is inspected to find a new sample C in the group with the greatest waveform value. Next data samples from a period of time equal to a scan interval centered in time about sample C are collected at step 72. The deviations of the data samples with respect to sample C, the one having the maximum value, are determined at step 74. If these deviations are found to be less than a maximum allowable deviation $\Delta$ at step 75, this respiratory segment is of sufficient quality (i.e. lacks extensive motion) to be used for updating the correlation kernel and the program advances to step 76. Otherwise, when the deviations exceed the maximum allowable deviation $\Delta$, the correlation kernel is not disturbed and the program execution returns to step 54 to acquire a new respiratory waveform sample.

When the program execution reaches step 76, the computer 26 counts back S samples from the maximum sample C to locate a new sample, $k_{end}$. Then a counter containing the value of n is incremented at step 78. Next the K waveform samples prior to and including the new sample $k_{end}$ are processed at step 80 to form a temporary correlation kernel $R_{temp}$ which then is weighted averaged with the previous kernel $R_{n-1}$ to form a new kernel $R_n$ at step 82. The averaging process weights the previous kernel more heavily than temporary correlation kernel $R_{temp}$ so that an atypical respiration cycle will not affect the correlation kernel significantly. Thereafter, the new kernel $R_n$ is used to determine the degree of fit of future sets of respiration waveform samples. In this manner, the averaging adapts the correlation kernel to variations in the aperiodic respiratory pattern of the patient.

The presently preferred method for predicting the approach of a quiescent period in respiration uses the adaptive moving correlation technique described above. This technique has been found to be satisfactory in predicting the end of inspiration far enough in advance so that the image acquisition interval (AI) will be centered about the end of inspiration. However, other adaptive techniques are available for utilizing acquired signal samples to predict future signal events. Two other adaptive techniques are least means squares and recursive least squares.

The least means squares (LMS) forms a prediction of future samples of the incoming respiration waveform based on a linear combination of past samples. The predicted samples are stored until corresponding real samples are acquired. The real data then is compared to the predicted samples and a error term is formed. The error term is employed to modify a set of tap weights such that the difference between the predicted samples and the real samples is minimized in the least squares sense. The linear combination of past samples is calculated from a product of the past samples and the tap weights. The rate at which the set of tap weights converge to the minimal least squares solution can be modified by parameters referred to as step size and misadjustment. Misadjustment is defined as the minimum difference between the predictor output and the least squares solution. Large step size increases the rate of convergence, but can lead to large misadjustment. Although this technique is very effective at predicting a few samples into the future, the LMS prediction converges very slowly beyond a few samples.

The recursive least squares (RLS) technique is similar to the least means square in that a set of tap weights are adaptively updated in order to minimize the error between the predictor output and the least squares solution. However, instead of waiting for the real samples to be acquired before updating the tap weights, the tap weight vector is estimated before the actual samples arrive. This estimation of the tap weight vector is recursively updated each time a new sample is acquired. Unlike LMS, where only a finite number of past samples are used, the recursive least squares process uses all previous samples, which allows for convergence rates an order of magnitude faster than LMS. While RLS has a prediction range farther into the future, it still is relatively unstable in the range for which predictions must be made to center the image data acquisition about the end of the inspiratory quiescent period, as compared to the preferred adaptive moving correlation method.

The present process has been applied to centering the acquisition interval AI about the end of inspiration, which produces a peak in the respiration signal. However, the process also can place image acquisition at the end of expiration which is indicated by valleys in the respiration signal waveform. In this latter instance, a signal minimum point can be used at steps 48 and 70 instead of a maximum point that was used to center acquisition about the end of inspiration.

The present invention has been described in terms of its application in a CT imaging system. However, similar needs exist to coordinate other medical imaging modalities with the respiration and other activity of the patient. Therefore, the present invention has applicability to other systems, such as magnetic resonance imaging and the X-ray apparatus.

The invention being claimed is:

1. A method for reducing artifacts in an image that result from motion of an object being imaged, where the image data is obtained during an acquisition interval, the motion having a quiescent period during which the motion is at a minimum; said steps of said method comprising:

producing a signal indicative of the motion;

defining a point in the signal such that if image acquisition commenced at that point a quiescent period would occur during an acquisition interval;

performing an analysis of a waveform shape of the signal which analysis uses an adaptive shape criterion that is updated over time based on information from the signal;

predicting from results of the analysis when a quiescent period is approaching; and commencing an image acquisition at a time prior to the predicted quiescent period so that the acquisition will occur during the quiescent period.

2. The method as recited in claim 1 wherein said step of analyzing a waveform shape of the signal utilizes either a least means square or a recursive least squares technique.

3. The method as recited in claim 1 wherein said step of analyzing a waveform shape of the signal utilizes adaptive moving correlation.

4. A method for reducing artifacts in an image that result from motion of an object being imaged, wherein image data is obtained during an acquisition interval, the motion having a quiescent period during which the motion is at a minimum; said steps of said method comprising:

producing a signal indicative of the motion;

selecting a first portion of the signal which occurs for a given time interval, such that a quiescent period will occur during the acquisition interval if image acquisition commenced at an end of the given time interval;

thereafter selecting subsequent portions of the signal, which occur during other time intervals;

comparing each selected subsequent portion to the reference signal portion and providing an descriptor of the similarity between the two portions; and commencing an image acquisition when the descriptor indicates a given degree of similarity.

5. The method as recited in claim 4 wherein said step of producing includes digitizing a signal indicative of the motion to produce a series of digital signal samples; and wherein said steps of selecting a first portion and selecting subsequent portions of the signal comprise selecting groups of digital signal samples.

6. The method as recited in claim 4 wherein said step of comparing utilizes either a least means square or a recursive least squares technique to produce the descriptor of the similarity.

7. The method as recited in claim 4 wherein said step of comparing utilizes an adaptive moving correlation process to produce the descriptor of the similarity.

8. The method as recited in claim 4 further comprising revising the reference signal portion by combining a previous reference signal portion with a selected subsequent portion.

9. A method for reducing artifacts in an image that result from motion of an object being imaged, wherein image data is obtained during an acquisition interval, the motion having a quiescent period that is shorter in duration that the acquisition interval and during which the motion is at a minimum; said steps of said method comprising:

(a) producing a signal indicative of the motion;

(b) locating a position in the signal which position occurs during a quiescent period;

(c) defining a point in the signal prior to the position such that if image acquisition commenced at that point a quiescent period would occur during an acquisition interval;

(d) selecting a first portion of the signal which occurred for a given interval of time prior to the defined point as a correlation kernel;

(e) thereafter selecting other portions of the signal which occur for periods of time having like duration to the given interval of time;

(f) comparing each another selected portion to the correlation kernel and providing an descriptor of the similarity between the two portions; and (g) commencing an image acquisition when a descriptor indicates a given degree of similarity.

10. The method as recited in claim 9 further comprising deriving a correlation kernel $R_{temp}$ from another selected portion; and revising the correlation kernel by combining the correlation kernel $R_{temp}$ with a previous correlation kernel.

11. The method as recited in claim 9 further comprising deriving a correlation kernel $R_{temp}$ from another selected portion; and revising the correlation kernel by averaging the correlation kernel $R_{temp}$ with a previous correlation kernel.

12. The method as recited in claim 11 wherein the averaging weights the previous correlation kernel more heavily than correlation kernel $R_{temp}$.

13. The method as recited in claim 9 further comprising:

periodically locating another position in the signal which other position occurs during a quiescent period;

defining another point in the signal prior to the other position such that if image acquisition commenced at that other point a quiescent period would occur during an acquisition interval;

selecting a section of the signal which occurred prior to the defined point as a temporary correlation kernel; and producing a revised correlation kernel by averaging the temporary correlation kernel with a previous correlation kernel, which revised correlation kernel then is used in the comparing step.

14. The method as recited in claim 9 wherein said step of producing a signal includes digitizing a signal indicative of the motion to produce a series of digital signal samples.

15. The method as recited in claim 13 wherein said step of defining a point in the signal involves counting a predefined number of signal samples from the position.

16. The method as recited in claim 13 wherein said steps of selecting a first portion and selecting other portions of the signal comprise selecting groups having a specified number of signal samples.

17. The method as recited in claim 9 wherein said step of locating a position in the signal which position occurs during a quiescent period comprises identifying a position at which the signal reaches a maximum level.

18. The method as recited in claim 9 wherein said step of locating a position in the signal which position occurs during a quiescent period comprises identifying a position at which the signal reaches a minimum level.

* * * * *